(12) United States Patent
Suzuki

(10) Patent No.: US 7,358,089 B2
(45) Date of Patent: Apr. 15, 2008

(54) PROCESS FOR PRODUCING A SUBSTRATE FOR ATTACHMENT OF CELLS

(75) Inventor: Shinji Suzuki, Tokyo-to (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 429 days.

(21) Appl. No.: 10/792,748

(22) Filed: Mar. 5, 2004

(65) Prior Publication Data

US 2004/0180435 A1 Sep. 16, 2004

(30) Foreign Application Priority Data

Mar. 11, 2003 (JP) ............................. 2003-065208

(51) Int. Cl.
*C12N 5/00* (2006.01)
*C12Q 1/02* (2006.01)
*C12M 3/00* (2006.01)

(52) U.S. Cl. ...................... 435/395; 435/29; 435/289.1

(58) Field of Classification Search ..................... None
See application file for complete search history.

(56) References Cited

U.S. PATENT DOCUMENTS 5,471,278 A 11/1995 Yasuda et al. ................ 355/67
6,312,864 B1 * 11/2001 Tokai et al. ................ 430/198
6,569,671 B1 5/2003 Okamoto et al. ......... 435/285.1
7,067,306 B2 * 6/2006 Singhvi et al. .......... 435/283.1

FOREIGN PATENT DOCUMENTS

JP 2001-324816 11/2001

* cited by examiner

*Primary Examiner*—David M. Naff
(74) *Attorney, Agent, or Firm*—David S. Safran

(57) ABSTRACT

A process for production of a substrate for attachment of cells at certain positions and a substrate for attachment of cells. A support structure comprising a hydrophobic resin base material and a hydrophilic polymer layer formed on the hydrophobic resin base material. Areas of the hydrophilic polymer layer and a chemical reaction product present on a boundary surface between the hydrophilic polymer layer and the hydrophobic resin base material are removed, so as to expose areas of the hydrophobic resin base material at which cells will attach, by irradiating the support structure with UV radiation emitted from a light source via a pattern mask. The exposed areas are depressions with a controlled shape matched to the mask pattern, each of the depressions having a bottom surface which is formed by exposure of the hydrophobic resin base material.

5 Claims, 2 Drawing Sheets

PROCESS FOR PRODUCING A SUBSTRATE FOR ATTACHMENT OF CELLS

BACKGROUND OF THE INVENTION

1. Field of the Invention

The invention relates to a process for producing a substrate for attachment of cells, in which cells can be attached, and a substrate for attachment of cells.

2. Description of the Prior Art

Recently in medicine and in agriculture and the like, biochemical studies have been promoted in which biomolecules such as, for example, nucleic acid and the like are treated as a research object.

In these studies, a substrate for attachment of biomolecules is produced, in which, for example, a plurality of biomolecules can be attached in an aligned state (see, for example, Japanese patent disclosure documents JP-A-2000-206702 (corresponding to U.S. Pat. No. 6,569,671 B1) and JP-A-2001-324816. Experiments, such as tests and syntheses of biomolecules and the like are carried out on this substrate for attachment of biomolecules.

Since recently not only biomolecules, such as nucleic acid and the like, but also cells are being treated as research objects, there is the demand that tests with respect to cells be carried out using a substrate in which the cells, as the research object, can be attached, such as a substrate for attachment of biomolecules. A process for simple production of a substrate for attachment of a plurality of cells in the aligned state is however not known.

SUMMARY OF THE INVENTION

The invention was devised to eliminate the above described defect in the prior art. Thus, a primary object of the present invention is to devise a process for simple production of a substrate for attachment of cells in which cells can be attached at certain positions. Another object of the invention is to devise a substrate for attachment of cells in which cells can be attached at certain positions.

The objects are achieved in accordance with the invention by a process for producing a substrate for attachment of cells in which a support structure is irradiated via a pattern mask with UV radiation which has been emitted from a light source, the support structure being obtained by formation of a hydrophilic polymer layer on the surface of a hydrophobic resin base material, and in which, in the UV irradiation area of the support structure which corresponds to the pattern of this pattern mask, the area of the hydrophilic polymer layer and the chemical reaction product are removed, which product is present on the boundary surface between this area of the hydrophilic polymer layer and the area of the hydrophobic resin base material layer of hydrophobic resin base material, so that a hydrophobic surface appears which originates from the hydrophobic resin base material.

The objects are furthermore advantageously achieved in accordance with the invention by a process in which the hydrophilic polymer layer is formed of polyacrylamide and the light source is a short arc lamp in which the arc tube is filled with at least cadmium and a rare gas and which has bright lines in a wavelength range from 200 to 230 nm.

The above state objects are also advantageously achieved in accordance with the invention by a process in which the substrate material, which has been obtained by the above mentioned process step for treatment of the support structure, is subjected to a surface treatment process step in which one of the following surface treatments (1) to (3) is carried out:

(1) UV irradiation treatment in which irradiation is carried out with UV radiation which is emitted from an excimer lamp or a low pressure mercury lamp, (2) oxygen-plasma treatment (3) inert gas-plasma treatment.

The objects are furthermore advantageously achieved in accordance with the invention by a process for producing a substrate for attaching cells in which depressions with a controlled shape are formed, each of which have a bottom surface which arises by the emergence of the hydrophobic surface.

Still further, the objects are achieved as in accordance with the invention by a substrate for attaching cells which is obtained by the above described process for producing a substrate for attachment of cells.

In the process of the invention for producing a substrate for attaching cells, the following is done:

A support structure is irradiated via a pattern mask with UV radiation, the support structure having a hydrophobic resin base material layer and a hydrophilic polymer layer; and the area of the hydrophilic polymer layer and the chemical reaction product which is present on the boundary surface between this area of the hydrophilic polymer layer and the area of the hydrophobic resin base material layer are removed in the UV irradiation area of the support structure which corresponds to this pattern mask so that a hydrophobic surface appears which originates from the hydrophobic resin base material.

This measure makes it possible to form a pattern by hydrophilic surface areas with the property that they will not adsorb cells, and by hydrophobic surface areas with the property of adsorbing cells such that, on this hydrophobic surface, there are cell capture areas at the desired locations in which cells are captured and attached. Therefore, a substrate for attachment of cells can be easily obtained in which cells can be attached at certain positions.

The invention is further described in detail below with reference to the accompanying drawings.

DETAILED DESCRIPTION OF THE INVENTION

The process in accordance with the invention for producing a substrate for attachment of cells is a process for forming a substrate in which cells can be attached and comprises a process step for treatment of a support structure in which a support structure is irradiated with UV radiation via a pattern mask, the support structure being obtained by formation of a hydrophilic polymer layer on the surface of a hydrophobic resin base material. Furthermore, the process of the invention for producing a substrate for attachment of cells, if necessary, has a process step for surface treatment in which the substrate material which was obtained in the process step for treatment of a support structure is subjected to a certain post-treatment.

The respective process step is described below.

(Process Step for Treatment of a Support Structure)

First, a solution of a hydrophilic polymer material which contains monomers, such as acrylamide or the like, is applied to the surface of a plate-shaped, hydrophobic resin base material with a thickness of, for example, 1 mm of a hydrophobic resin such as, for example, polystyrene or the like. The resulting film is irradiated, for example, with electron beams. In this way, the hydrophilic polymer material (in this example, acrylamide) is subjected to polymerization, and thus, a hydrophilic polymer layer 12 with a thickness of, for example, 20 nm is formed.

Figure 1:
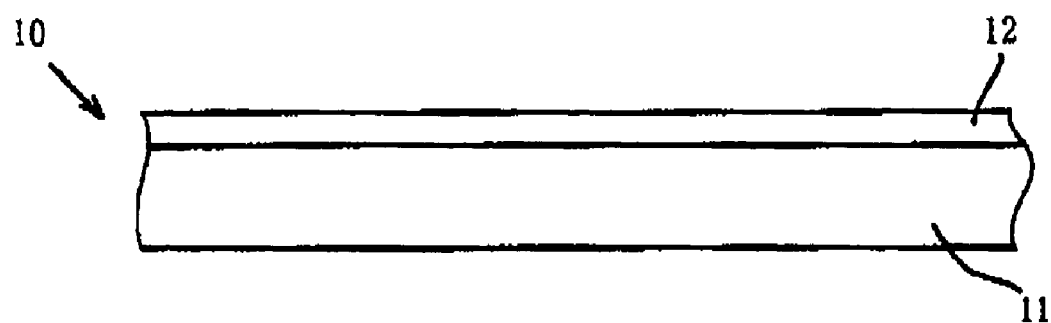
FIG. 1 shows a hydrophilic polymer layer formed on a hydrophobic resin base material.

In this way, a support structure 10 (hereinafter also called a "certain support structure") is obtained in which a hydrophobic resin base material layer 11 of a hydrophobic resin base material and a hydrophilic polymer layer 12 come to rest on top of one another, as is shown in FIG. 1. In this certain support structure 10, on the boundary surface between the hydrophobic resin base material layer 11 and the hydrophilic polymer layer 12, there is a chemical reaction product which was produced by the reaction of the hydrophilic polymer material with the hydrophobic resin comprising the hydrophobic resin base material on the boundary surface between the film on which application was carried out and the hydrophobic resin base material in the polymerization of the hydrophilic polymer material comprising the above described film with the application.

Figure 2:
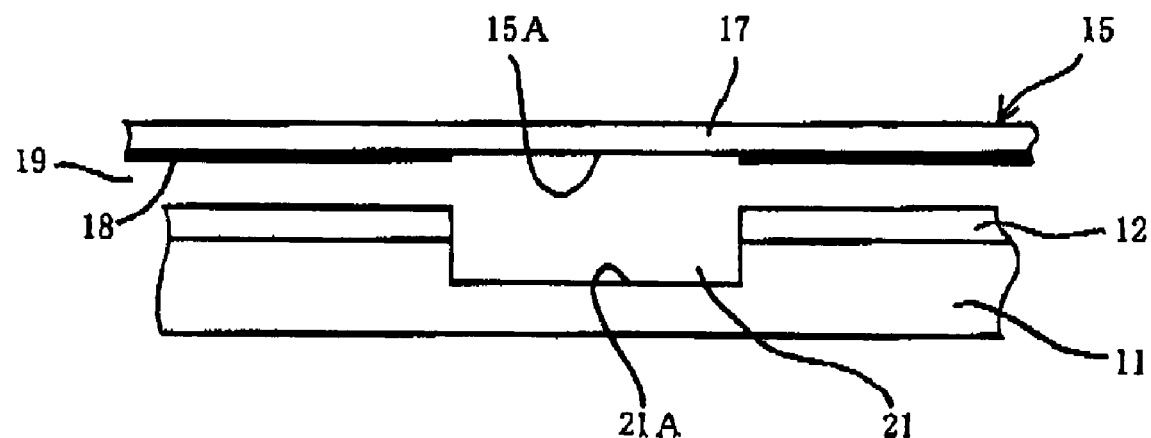
FIG. 2 shows a schematic cross section of the state in which a depression is formed by irradiation of a support structure with UV radiation which is emitted from a light source.

Next, as shown in FIG. 2, there is a light source lamp (not shown in this figure) and a pattern mask 15 located above (top in FIG. 2) the hydrophilic polymer later 12 which forms the certain support structure 10. The mask 15 is formed with a pattern of openings 15A (hereinafter also called a "certain opening pattern"). Each opening 15A corresponds in its position and its shape to a cell capture area. In these cell capture areas of the substrate which is to be ultimately obtained, cells are attached. The pattern mask 15 is placed at a given position of the area 19 which is located between the hydrophilic polymer layer 12 of the certain support structure 10 and the light source lamp.

The light source lamp is shifted into the operating state and via the pattern mask 15 irradiates the certain support structure 10 with UV radiation which is emitted from the light source lamp onto the surface (upper side in FIG. 2) of the hydrophilic polymer layer 12.

As is shown in FIG. 2, by this irradiation of the certain support structure 10 with UV radiation via the pattern mask 15, for this certain support structure 10; an area which corresponds to the opening 15A of the pattern mask 15 is selectively irradiated with UV radiation. In the UV irradiation range which corresponds to a certain opening pattern of this pattern mask 15, the hydrophilic polymer layer area and the chemical reaction product which is present underneath this hydrophilic polymer layer area are removed. Furthermore, if necessary, the surface layer area of the hydrophobic resin base material layer 11 is removed, by which extremely small depressions 21 with a depth of, for example, 100 nm (hereinafter also called an "extremely small depression") are formed in the certain support structure 10 according to the certain opening pattern of the pattern mask 15, the depressions 21 each having a bottom area 21A. This bottom area 21A is in the state in which the hydrophobic surface emerges which originates from the hydrophobic resin base material which forms the hydrophobic resin base material layer 11.

A substrate material 20 has the extremely small depressions 21 which have been obtained in the process step for treatment of the support structure. When all of the extremely small depressions which have formed in the substrate material 20 are in the state in which the hydrophobic surface emerges completely on the entire area of the bottom areas 21A, each of these extremely small depressions 21 on the overall area of the bottom area 21A can adsorb a cell. Therefore sufficient cell capture efficiency can be obtained. These extremely small depressions 21 are therefore active in the unaltered state as cell capture areas and can therefore be used as the substrate for attachment of cells in which cells are attached in these cell capture areas.

Figure 3:
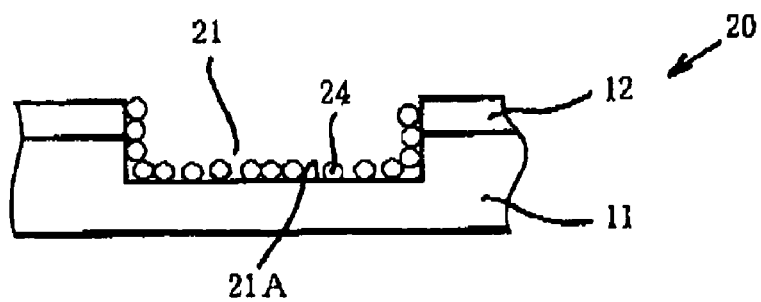
FIG. 3(a) is a schematic cross-sectional view showing adhesion of hydrophilic material in the depression of the substrate material.
FIG. 3(b) shows a layer which is formed covering the surface of the depression.
Figure 3:
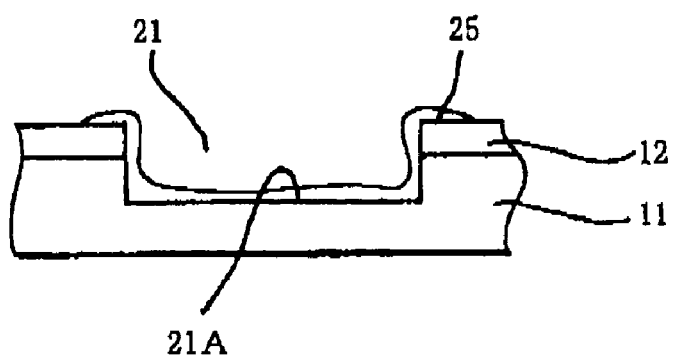

However, as shown in FIG. 3(a), there are cases in which material 24 which originates from the hydrophilic polymer layer or from the chemical reaction product which have been removed by ablation adheres again on the surface of the extremely small depression 21. Furthermore, there are cases in which, as shown in FIG. 3(b), a byproduct which originates from the material 24 adheres again on the surface of the extremely small depression 21, forming a layer 25 which covers part or all of the surface of this extremely small depression 21 (in FIG. 3b, a layer is shown which covers the entire surface of the depression 21). Or there are cases in which the substrate material 20 has extremely small depressions 21 in which part or all of the bottom area 21A does not completely emerge because the chemical reaction product is not completely removed and therefore remains, or for similar reasons.

For this reason, it is advantageous that after the process step of treatment of the support structure, in addition, a post-treatment is carried out for elimination of the above described adhering material 24 or the layer 25, composed of the remaining chemical reaction product and the like.

(Process Step for Surface Treatment)

Figure 4:
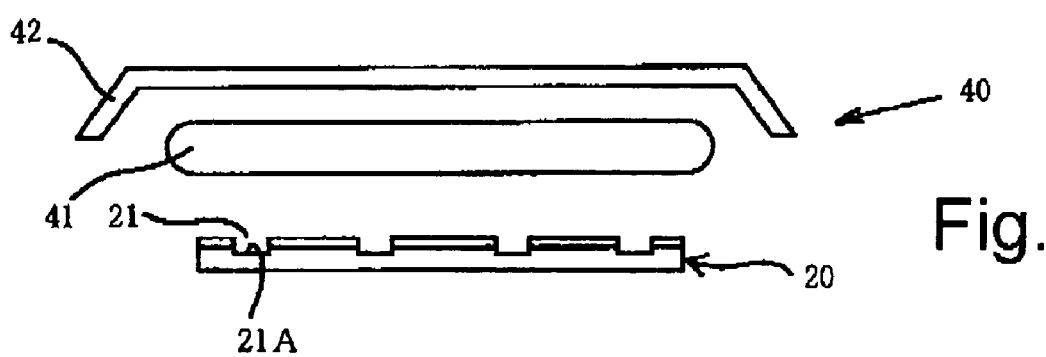
FIG. 4 shows a schematic cross section of the substrate material and a lamp device for surface treatment which has a lamp and a reflector.

As is shown in FIG. 4, if above the substrate material 20 (top in FIG. 4), there is a lamp device 40 for surface treatment which has a lamp 41, such as an excimer lamp or a low pressure mercury lamp, and a reflector 42, in an atmosphere which contains oxygen or ozone, such as air or the like, this lamp 41 for surface treatment is operated such that the illuminance at a wavelength of 172 nm is 10 mW/cm$^2$ if, for example, the lamp 41 for surface treatment is an excimer lamp. In an atmosphere which contains oxygen or ozone, such as for example, air or the like, this lamp 41 for surface treatment is operated, for example, such that the illuminance with respect to a wavelength of 185 nm is 15 mW/cm$^2$ if the lamp 41 for surface treatment is a low pressure mercury lamp. The entire area (top side in FIG. 4) on which the extremely small depressions 21 of the substrate material 20 are formed is irradiated at the same time with UV radiation which is emitted from the lamp 41 for surface treatment for a few seconds, for example.

In this treatment, active oxygen is formed by the action of the UV radiation on the oxygen or the ozone. By the contact of this active oxygen with the coating material, the material which coats the coating material is incinerated in an oxidation reaction by the active oxygen and removed. For this reason, in the substrate material 20, all of the extremely small depressions 21 are in the state in which the hydrophobic surface emerges completely on the entire area of the respective bottom area 21A.

As was described above, by carrying out the process step for treatment of the support structure and by the process step for surface treatment which is carried out, if necessary, a substrate 30 for attachment of cells (in FIG. 5) is formed which has a hydrophilic surface of the hydrophilic polymer layer 12 and cell capture areas 31 which are formed of the extremely small depressions 21 with a bottom area 21A, the depressions 21 being formed in the desired pattern shape according to the certain opening pattern of the pattern mask 15 and the bottom area 21A being in the state in which the hydrophobic surface emerges.

Polystyrene can be advantageously used as the hydrophobic resin base material. However, for example, polyethylene terephthalate or the like can also be used. It is normally advantageous for the thickness of the hydrophobic resin base material to be 0.5 mm to 3 mm.

The solution which contains the hydrophilic polymer material can be a solution which is formed by dissolving a hydrophilic polymer material in a solvent such as water, ethanol, or the like, for example. Acrylamide can be advantageously used as the hydrophilic polymer.

For the certain support structure 10, it is desirable for the thickness of the hydrophilic polymer layer 12 to be normally 50 nm to 500 nm.

The light source lamp can be a lamp which emits UV radiation. Specifically, a lamp can be advantageously used which has bright lines, for example, at least at one of the wavelengths of roughly 214 nm, roughly 215 nm, roughly 219 nm, and roughly 220 nm, especially at one of the wavelengths of roughly 214 nm and 219 nm.

When the certain support structure 10 has a hydrophilic polymer layer 12 of polyacrylamide, it is desirable for the light source to be a short arc lamp in which the arc tube is filled at least with cadmium and a rare gas, and which has bright lines in the wavelength range from 200 nm to 230 nm. This short arc lamp can be, for example, the arrangement which was disclosed in Japanese patent specification No. 3020397 (corresponding to U.S. Pat. No. 5,471,278).

The pattern mask 15 can be, for example, a filter in which a film 18, which has been produced by evaporation of a metal, is formed on a transparent substrate 17 and has a certain opening pattern. The outside diameter of the opening 15A for the pattern mask 15 is normally 30 microns to 50 microns, although depending on the type of cells which the substrate 30 is to attach and depending on the number of cells which are to be attached in a single cell attachment area 31 and the like, it is different because it corresponds to the outside diameter of the extremely small depressions 21 which form the cell capture areas 31 of the substrate 30 which is to be ultimately obtained for attachment of cells.

The lamp 41 is an excimer lamp or a low pressure mercury lamp. However, specifically, an excimer lamp which has bright lines at a wavelength of 172 nm, and a low pressure mercury lamp which has bright lines at a wavelength of 185 nm can be advantageously used.

The following measures are taken by the above described process for producing a substrate for attachment of cells.

The certain support structure 10 which has the hydrophobic resin base material layer 11 and the hydrophilic polymer layer 12 is irradiated via the pattern mask 15 in which a certain opening pattern is formed with the UV radiation which has been emitted from the light source. In this way, in the UV irradiation area of the certain support structure 10 which corresponds to a certain opening pattern, the area of the hydrophilic polymer layer and the chemical reaction product which is present on the boundary surface between this area of the hydrophilic polymer layer and the area of the hydrophobic resin base material layer are removed. Furthermore, the surface layer area of the hydrophobic resin base material layer 11 is removed so that a hydrophobic surface appears. In this way, in the certain support structure 10 with a hydrophilic surface which formed of the hydrophilic polymer layer 12 and which has the property that cells are not adsorbed, the cell capture areas 31 can be formed from the extremely small depressions 21 with the bottom areas 21A in the desired pattern shape according to the certain opening pattern of the pattern mask 15, the respective bottom area 21A being in the state in which the hydrophobic surface with the property of adsorbing cells emerges. Therefore a substrate 30 for attachment of cells can be easily obtained in which cells can be attached at certain positions from these cell capture areas 31.

Especially by carrying out the process step for surface treatment can extremely small depressions 21 which have been formed in the process step for treatment of the support structure be shifted into the state in which the hydrophilic surface emerges completely on the entire area of the respective bottom area 21A. The substrate 30 for attachment of cells which is ultimately obtained can therefore adsorb cells on the overall area of the respective bottom area 21A of the extremely small depressions 21 comprising all the cell capture areas 31. Therefore, a substrate 30 for attachment of cells can be obtained in which the cell capture areas 31 have sufficient cell capture efficiency and cells can be captured with certainty.

Furthermore, for example, by controlling the thickness of the hydrophilic polymer layer 12 of the certain support structure 10 which is used in the process step for treatment of the support structure, by controlling the shape of the opening 15A of the pattern mask 15 which is used in the process step for treatment of the support structure, by controlling the UV irradiation conditions for a certain support structure 10 in the process step for treatment of the support structure or by similar measures the extremely small depressions 21 can be formed in a controlled shape and in this way it becomes possible for the substrate 30 which has finally been obtained for attachment of cells at certain positions which consist of the cell capture areas 31 to attach a certain number of cells.

Figure 5:
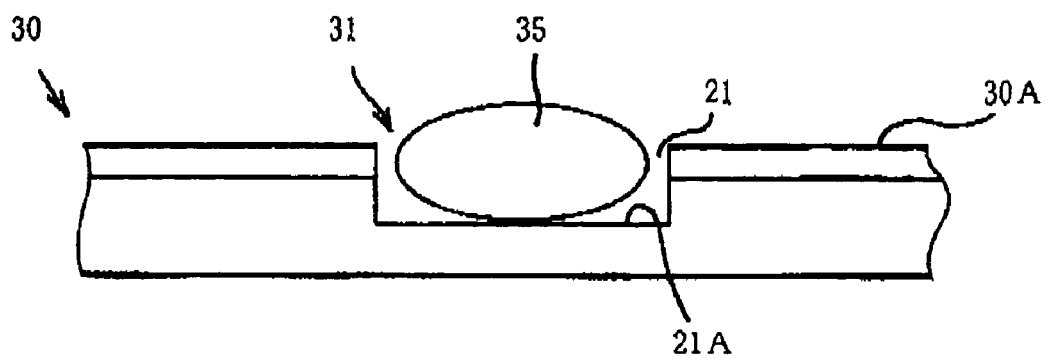
FIG. 5 is a schematic cross section in which in the cell capture area of a substrate in accordance with the invention has a cell captured and attached.

Specifically, as shown in FIG. 5, extremely small depressions 21 can be formed with a shape which is controlled such that they have an outside diameter which is matched to the size of the cell 35 which is to be attached (hereinafter also called the "object cell") and that they have a depth by which, when the object cell 35 is captured and attached by the cell capture area 31 which comprises an extremely small depression, this object cell 35 projects over the surface 30A (top side in FIG. 5) of the substrate 30 for attachment of cells. This measure makes it possible for the substrate 30 for attachment of cells which has been finally obtained to attach an object cell in its cell capture area 31.

The substrate 30 which is obtained by this production process for attachment of cells can specifically attach cells at certain positions at which the cell capture areas 31 are formed. Therefore, several cells can be attached, for example, in an aligned state.

Specifically, the respective object cells do not remain on the surface 30A of the hydrophilic surface which has the property of not adsorbing cells when, for a substrate 30 on which several cell capture areas 31 are formed, physiological saline solution which contains a plurality of the cells which are to be attached (hereinafter also called "object cells") is dripped, for example, onto this substrate 30. The object cells are captured in the extremely small depressions 21 with the bottom areas 21A on which the hydrophobic surfaces of the cell capture areas 31 emerge by contact with these bottom areas 21A, and thus, are attached in these cell capture areas 31.

Here, if the respective extremely small depression 21 comprising the individual cell capture area 31 is formed in a controlled shape and it has a shape which is matched to a certain number of the object cells which are to be attached, it never happens that more than that certain number of object cells are attached in these cell capture areas.

Preferred embodiments of the invention have been described above, but various modifications can be added to the invention. For example, in the process step for surface treatment, the surface treatment can be carried out with low costs because a vacuum condition is not needed. It is advantageous to use a method in which the coating material is eliminated by oxidation-cleaning treatment by means of UV radiation using an excimer lamp or a low pressure mercury lamp. However, the coating material can also be removed from the substrate material by the above described method (A) or (B) and all extremely small depressions can be shifted into the state in which the hydrophobic surface emerges on the entire areas of the bottom areas.

(A) Method in which the substrate material is exposed to an oxygen-plasma atmosphere and is subjected to plasma treatment and in which, in this way, the coating material is eliminated by a chemical cleaning treatment.

(B) Method in which the substrate material is exposed to an inert gas-plasma atmosphere such as, for example, argon gas-plasma or the like and is subjected to plasma treatment and in which the coating material is physically removed.

Action of the Invention

In the process of the invention for production of a substrate for attachment of cells, a process step is carried out in which a support structure with a hydrophobic resin base material layer and a hydrophilic polymer layer is irradiated with UV radiation via a pattern mask, and in which the area of the hydrophilic polymer layer and the chemical reaction product present on the boundary surface between this area of the hydrophilic polymer layer and the area of the hydrophobic resin base material layer are removed in the UV irradiation area of the support structure which corresponds to this pattern mask, so that a hydrophobic surface appears which originates from the hydrophobic resin base material. This measure makes it possible to form a pattern which is formed by hydrophilic surface areas with the property of not adsorbing cells, and by hydrophobic surface areas with the property of adsorbing cells such that on this hydrophobic surface there are cell capture areas for capturing and attaching cells at the desired locations. Therefore, a substrate for attachment of cells can be easily obtained in which cells can be attached at certain positions.

By the production process with a process step for surface treatment, the substrate material which was obtained in the process step for treatment of the support structure is subjected to a certain treatment. In this way, the material coating the hydrophobic surface is removed. This hydrophobic surface can thus emerge completely. Therefore, the possible result is that for the substrate which has finally been obtained for attachment of cells all the cell capture areas have sufficient cell capture efficiency with certainty.

The substrate of the invention for attachment of cells has hydrophilic surface areas with the property that cells are not adsorbed, and hydrophobic surface areas with the property that cells are adsorbed. Cell capture areas in which cells are captured and attached are formed in the shape of the desired patten on this hydrophobic surface. Therefore, cells can be attached at certain positions.

What is claimed is:

1. Process for producing a substrate for attachment of cells, comprising the following process steps:
   providing a support structure comprising a hydrophobic resin base material, a hydrophilic polymer layer formed on the hydrophobic resin base material, and a chemical reaction product on a boundary surface between the hydrophilic polymer layer and the hydrophobic resin base material produced by reaction of the hydrophilic polymer material with hydrophobic resin of the hydrophobic resin base material;
   irradiating the support structure with UV radiation emitted from a light source via a pattern mask, UV irradiation of the support structure corresponding to the pattern of the pattern mask removing areas of the hydrophilic polymer layer and the chemical reaction product present on the boundary surface between the hydrophilic polymer layer and the hydrophobic resin base material so that the areas of the hydrophobic resin base material are exposed to produce said substrate for attachment of cells;
   wherein, following the providing and irradiating steps, the substrate produced is subjected to a surface treatment process step in which one of the following surface treatments (1) to (3) is carried out for removal of any material originating from at least one of the hydrophilic polymer layer and the chemical reaction product which have been removed, or any by product thereof, that has adhered to the exposed areas of the hydrophobic resin base material:
   (1) UV irradiation treatment in which irradiation is carried out with UV radiation which is emitted from an excimer lamp or a low pressure mercury lamp,
   (2) oxygen-plasma treatment,
   (3) inert gas-plasma treatment.

2. Process for producing a substrate for attachment of cells, comprising the following process steps:
   providing a support structure comprising a hydrophobic resin base material, a hydrophilic polymer layer formed on the hydrophobic resin base material, and a chemical reaction product on a boundary surface between the hydrophilic polymer layer and the hydrophobic resin base material produced by reaction of the hydrophilic polymer material with hydrophobic resin of the hydrophobic resin base material;
   irradiating the support structure with UV radiation emitted from a light source via a pattern mask, UV irradiation of the support structure corresponding to the pattern of the pattern mask removing areas of the hydrophilic polymer layer and the chemical reaction product present on the boundary surface between the hydrophilic polymer layer and the hydrophobic resin base material so that the areas of the hydrophobic resin base material are exposed to produce said substrate for attachment of cells;
   wherein the hydrophilic polymer layer is polyacrylamide and that the light source is a short arc lamp in which the arc tube is filled with at least cadmium and a rare gas and which produces bright lines in a wavelength range from 200 to 230 nm.

3. Process for producing a substrate for attachment of cells as claimed in claim 2, wherein, following the providing and irradiating steps, the substrate produced is subjected to a surface treatment process step in which one of the following surface treatments (1) to (3) is carried out for removal of any material originating from at least one of the hydrophilic polymer layer and the chemical reaction product which have been removed, or any by product thereof, that has adhered to the exposed areas of the hydrophobic resin base material:
   (1) UV irradiation treatment in which irradiation is carried out with UV radiation which is emitted from an excimer lamp or a low pressure mercury lamp,
   (2) oxygen-plasma treatment,
   (3) inert gas-plasma treatment.

4. Process for producing a substrate for attachment of cells as claimed in claim 3, wherein depressions with a controlled shape are formed, each of which have a bottom surface which is formed by said exposure of the hydrophobic resin base material.

5. Process for producing a substrate for attachment of cells as claimed in claim 1, wherein depressions with a controlled shape are formed, each of which has a bottom surface which is formed by emergence of a surface of the hydrophobic resin base material as a result of the removal of areas of the hydrophilic polymer layer and the chemical reaction product.

* * * * *